(12) United States Patent
Reiffenrath et al.

(10) Patent No.: US 6,444,278 B1
(45) Date of Patent: *Sep. 3, 2002

(54) 2,6-DI-TERT-BUTYLPHENOLS

(75) Inventors: Volker Reiffenrath, Darmstadt (DE); Joachim Krause, Darmstadt (DE)

(73) Assignee: Merck Patent Gesellschaft Mit Beschraenkter Haftung (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/948,521

(22) Filed: Oct. 10, 1997

Related U.S. Application Data

(63) Continuation of application No. 08/732,717, filed on Oct. 18, 1996, now abandoned.

(30) Foreign Application Priority Data

Oct. 20, 1995 (DE) .......................... 195 39 411

(51) Int. Cl.[7] .................. C09K 19/54; C09K 19/34; C07C 69/76; C07C 39/06; C07D 239/02; C07D 319/06
(52) U.S. Cl. .............. 428/1.1; 252/299.61; 252/299.63; 252/299.5; 544/298; 544/336; 549/369; 560/67; 560/75; 568/784
(58) Field of Search ..................... 252/299.01, 299.5, 252/299.61, 299.63, 407; 560/67, 75; 568/784; 549/369; 544/298, 336; 428/1.1

(56) References Cited

U.S. PATENT DOCUMENTS

| | | | | |
|---|---|---|---|---|
| 3,206,431 | A | * 9/1965 | Doyle et al. | 524/288 |
| 4,172,151 | A | 10/1979 | Moore | 514/647 |
| 5,185,097 | A | * 2/1993 | Toshida et al. | 252/299.01 |
| 5,252,251 | A | * 10/1993 | Sato et al. | 252/299.01 |

FOREIGN PATENT DOCUMENTS

DE 2109304 * 9/1971

OTHER PUBLICATIONS

CA 121: 135315, 1994.*
CA 122: 160175, 1994.*
CA 123: 169375, 1995.*
CA 90: 55645, 1978.*
CA 89: 42858, 1978.*
CA 88: 23774, 1977.*
CAPLUS:508107, 1994.*
CAPLUS 1989:38678, 1989.*
Boy et al. "Electrosynthesis of Unsymmetrical Polyaryls by a SRN1—Type Reaction", J. Org. Chem., vol. 59, No. 16, 1994.*
CA 76:46888, 1972.*
CA 91: 174527, 1979.*
CA 109: 192103, 1988.*
CAPLUS 1971: 111651.*
CA 123: 313466, 1994.*
Lazer et al., "Antiinflammatory 2,6–Di–tert–butyl–4–(2–arylethenyl) phenols", J. Med. Chem, 1989, 32, pp. 100–104.
CAPLUS Abstract of Russian article "Electronic structure of antitumor activity of the ionol . . . ". 1988: 447922.
CAPLUS Abstract of Russian article "Arylatio nof aromatic hydrocarbons during thermal . . . ", 1968: 467034.

* cited by examiner

Primary Examiner—Shean C. Wu
(74) Attorney, Agent, or Firm—Millen, White, Zelano & Branigan, P.C.

(57) ABSTRACT

The present invention relates to 2,6-di-tert-butylphenols of the formula I

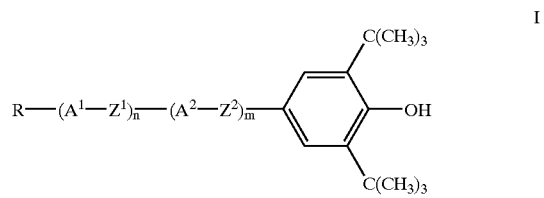

in which
R, $A^1$ $A^2$, $Z^1$, $Z^2$ m and n are as defined herein, and their use as stabilizers or antioxidants.

10 Claims, No Drawings

2,6-DI-TERT-BUTYLPHENOLS

This application is a continuation, of application Ser. No. 08/732,717, filed Oct. 18, 1996, now abandoned.

The present invention relates to 2,6-di-tert-butylphenols of the formula I

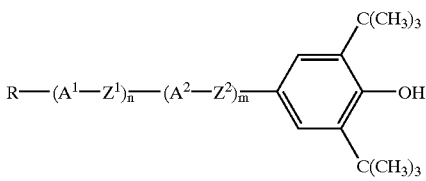

in which

R is H, an alkyl or alkenyl radical having 1 to 18 carbon atoms which is unsubstituted or substituted by CN or by at least one halogen, e.g., up to perhalo-substituted, and in which one or more non-adjacent $CH_2$ groups may be replaced by a radical selected from the group consisting of —O—, —S—, —CO—, —O—CO—, —CO—O— and —C≡C—, $A^1$ and $A^2$ are, independently of one another,
  a) a 1,4-phenylene radical, in which one or two CH groups may be replaced by N,
  b) a 1,4-cyclohexenylene or 1,4-cyclohexylene radical, in which one or two non-adjacent $CH_2$ groups may be replaced by —O— or —S—,
  c) a piperidine-1,4-diyl, a 1,4-bicyclo[2.2.2]-octylene or naphthalene-2,6-diyl radical,
  where the radicals a) and b) may be monosubstituted or polysubstituted by halogen atoms, $Z^1$ and $Z^2$ are each, independently of one another, —CO—O—, —O—CO—, —$CH_2$—O—, —O$CH_2$—, —$CH_2CH_2$—, —CH=CR—, —C≡C— or a single bond, and m and n are each, independently of one another, 0, 1, 2 or 3, where m+n≧1, with the proviso that compounds of the formulae

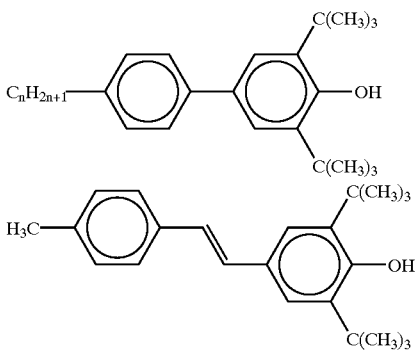

where n = 1–3 are excluded.

BACKGROUND OF THE INVENTION

Since autoxidation can result in a considerable drop in value of many natural products, for example foodstuffs and natural rubber, and, industrial products, for example monomers for polymerization purposes, petroleum products and plastics, the search for substances which prevent or retard autoxidation in the lowest possible concentration has become a broad area of research.

The phenolic antioxidants used today in industry are phenols which are substituted in the ortho-position to the hydroxyl group, usually by bulky groups. The action of these sterically hindered phenols is based on the ready liberation of the phenolic hydrogen atom with formation of phenoxide free radicals.

The use of antioxidants relates essentially to the stabilization of oils, fats and plastics. Antioxidants for these purposes must not be toxic, should have high effectiveness at low concentrations, should not cause any changes in taste, odor or color, even on extended storage or heating, should be readily soluble or easily dispersible in the substrate, should not exert any adverse effect on the substance to be protected, should have low volatility, and should allow analytical determination as quantitatively as possible.

Furthermore, antioxidants should be simple and inexpensive to prepare, and their handling and incorporation should be simple.

The prior art contains phenolic antioxidants of the formulae

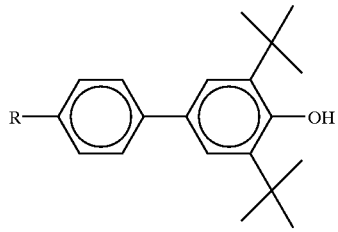

U.S. 4, 172, 151
Izv. Akad. Nauk SSSR, Ser. Khim. (1968) 204–6
R = H, $NH_2$, $NHCOCF_3$, $CH_3$, $C_2H_5$, i-$C_3H_7$

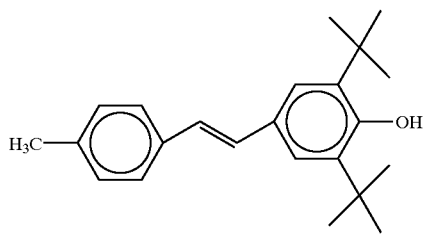

J. Med. Chem. (1989), 32(1), 100–4

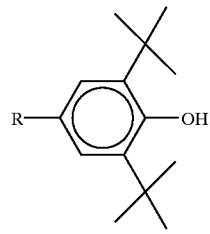

Vest. Mosk. Univ. Ser. 2: Khim (1988), 29(2), 167–72
R = H, $CH_3$, $OCH_3$, $CH_2OCH_3$, $CH_2Ph$, Ph, $C_6H_4$Me-4, $C_6H_4$OMe-4, naphthyl However, the antioxidants mentioned do not satisfy all requirements. A particular disadvantage is that the antioxidants mentioned must be employed in relatively high concentrations.

SUMMARY OF THE INVENTION

An object of the present invention was therefore to find inexpensive antioxidants which satisfy all the conditions mentioned.

Upon further study of the specification and appended claims, further objects and advantages of this invention will become apparent to those skilled in the art.

Surprisingly, it has now been found that the 2,6-di-tert-butylphenols of the formula I have high effectiveness as antioxidants, even at low concentrations, without exerting any adverse effect on the substance to be protected. Furthermore, the novel sterically hindered phenols are distinguished by heat resistance, low viscosity and low volatility.

The invention thus relates to 2,6-di-tert-butylphenols of the formula I.

The claimed compounds are free-radical scavengers and are therefore suitable for suppressing ageing processes caused by free-radical chain reactions, such as, for example, autoxidation.

Owing to their structure, these materials have a particularly low vapor pressure and can thus also be employed at high temperatures. They and their reaction products are colorless and thus do not result in any discoloration of the materials to be stabilized.

For reasons of simplicity, phenol below denotes

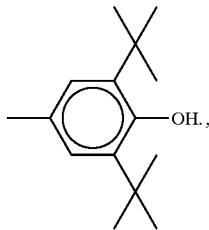

Cyc denotes a 1,4-cyclohexylene radical, Che denotes a 1,4-cyclohexenylene radical, Dio denotes a 1,3-dioxane-2,5-diyl radical, Dit denotes a 1,3-dithiane-2,5-diyl radical, Phe denotes a 1,4-phenylene radical, Pyd denotes a pyridine-2,5-diyl radical, Pyr denotes a pyrimidine-2,5-diyl radical and Bi denotes a bicyclo[2.2.2]octylene radical, where Cyc and/or Phe may be unsubstituted or monosubstituted or disubstituted by F.

The compounds of the formula I accordingly include bicyclic compounds of the subformulae Ia and Ib:

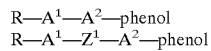

| | |
|---|---|
| R—$A^1$—$A^2$—phenol | Ia |
| R—$A^1$—$Z^1$—$A^2$—phenol | Ib | tricyclic compounds of the subformulae Ic to Ig:

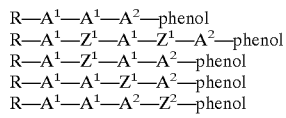

| | |
|---|---|
| R—$A^1$—$A^1$—$A^2$—phenol | Ic |
| R—$A^1$—$Z^1$—$A^1$—$Z^1$—$A^2$—phenol | Id |
| R—$A^1$—$Z^1$—$A^1$—$A^2$—phenol | Ie |
| R—$A^1$—$A^1$—$Z^1$—$A^2$—phenol | If |
| R—$A^1$—$A^1$—$A^2$—$Z^2$—phenol | Ig | and tetracyclic compounds of the subformulae Ih to Io:

| | |
|---|---|
| R—$A^1$—$A^1$—$A^1$—$A^2$—phenol | Ih |
| R—$A^1$—$Z^1$—$A^1$—$A^1$—$A^2$—phenol | Ii |
| R—$A^1$—$A^1$—$Z^1$—$A^1$—$A^2$—phenol | Ij |
| R—$A^1$—$A^1$—$A^1$—$Z^1$—$A^2$—phenol | Ik |
| R—$A^1$—$Z^1$—$A^1$—$Z^1$—$A^1$—$A^2$—phenol | Il |
| R—$A^1$—$Z^1$—$A^1$—$A^1$—$Z^1$—$A^2$—phenol | Im |
| R—$A^1$—$A^1$—$Z^1$—$A^1$—$Z^1$—$A^2$—phenol | In |
| R—$A^1$—$Z^1$—$A^1$—$Z^1$—$A^1$—$Z^1$—$A^2$—phenol | Io |

Of these, particular preference is given to those of the subformulae Ia, Ib, Ic, Id, Ie and If.

In the compounds of the formula I, $Z^1$ and $Z^2$ are preferably a single bond or $CH_2CH_2$, secondarily preferably —$CH_2O$—, —$OCH_2$—, —O—CO— or —CO—O—.

If one of the radicals $Z^1$ and $Z^2$ is —$(CH_2)_4$— or —CH=CH—$CH_2CH$—, the other radical $Z^1$ or $Z^2$ (if present) is preferably a single bond.

The sun n+m is preferably 1 or 2.

If R is an alkyl radical and/or an alkoxy radical, this can be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl, i.e., having a $CH_2$ group replaced by —O—, is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If R is an alkyl radical in which one $CH_2$ group has been replaced by —CH=CH—, this can be straight-chain or branched. It is preferably straight-chain and has 2 to 10 carbon atoms. Accordingly, it is in particular vinyl, prop-1- or -2-enyl-, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, 5-, -6-, -7-, -8- or -9-enyl.

If R is an alkyl radical in which one $CH_2$ group has been replaced by —O— and one has been replaced by —CO—, these are preferably adjacent. These thus contain one acyloxy group —CO—O— or one oxycarbonyl group —O—CO—. These are preferably straight-chain and have 2 to 6 carbon atoms.

Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If R is an alkyl radical in which one $CH_2$ group has been replaced by unsubstituted or substituted —CH=CH— and an adjacent $CH_2$ group has been replaced by CO or CO—O or O—CO—, this can be straight-chain or branched. It is preferably straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl and 9-methacryloyloxynonyl.

If R is an alkyl or alkenyl radical which is at least monosubstituted by halogen, this radical is preferably straight-chain and halogen is preferably F or Cl. In the case of multiple substitution, halogen is preferably F. The resultant radicals also include perfluorinated radicals. In the case of monosubstitution, the fluorine or chlorine substituent can be in any desired position, but is preferably in the ω-position.

Branched radicals R generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

If R is an alkyl radical in which two or more $CH_2$ groups have been replaced by —O— and/or —CO—O—, this may be straight-chain or branched. It is preferably branched and has 3 to 12 carbon atoms. Accordingly, it is in particular biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl and 5,5-bis(ethoxycarbonyl)pentyl.

Preferred subgeneric groups of compounds of the formula I are those of the subformulae I1 to I10

I9

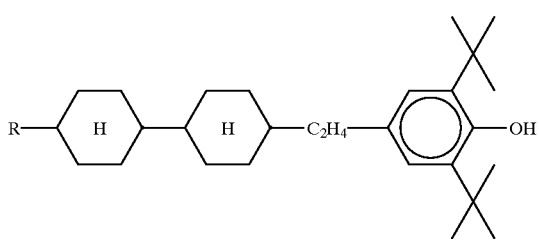

I10

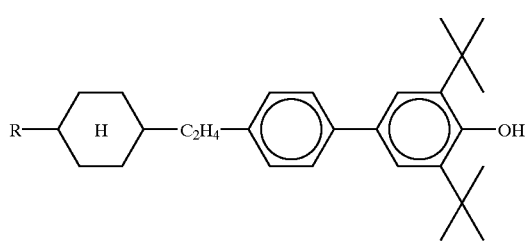

Particular preference is given to the compounds of the formulae I1 and I2.

The compounds of the formula I are prepared by methods known per se, as described in the literature (for example in the standard works such as Houben-Weyl, Methoden der Organischen Chemie, Georg Thieme Verlag, Stuttgart), to be precise under reaction conditions which are known and suitable for said reactions. Use can also be made here of variants which are known per se, but are not mentioned here in greater detail.

The novel compounds can be prepared, for example, in accordance with Schemes 1 and 2:

Scheme 1

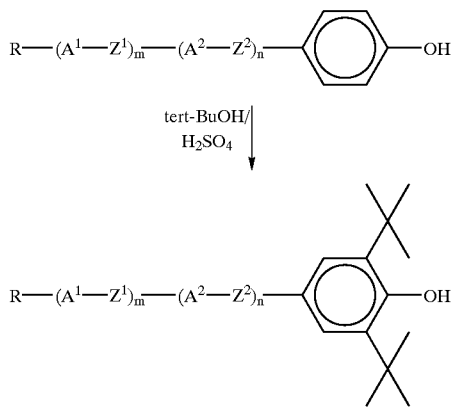

Scheme 2

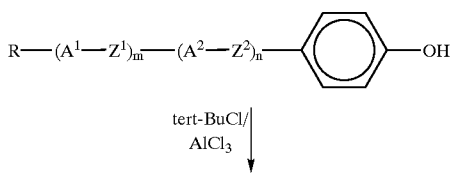

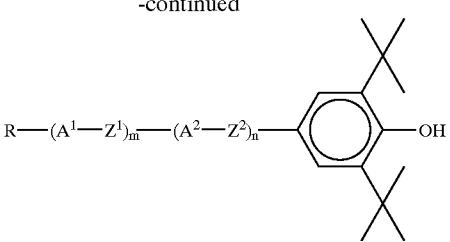

The compounds of the formula I have a broad range of applications. They can easily be used as stabilizers in the foods sector and in industrial products.

The invention also relates to the use of the novel compounds as additives for liquid-crystal mixtures, liquid-crystalline individual components, lubricants, heat-transfer media, fuels, pharmaceutical products, vitamin preparations, cosmetics, foodstuffs, dyes, paints, polymers, elastomers, detergents, solvents, paper and crop-protection agents.

The compounds of the formula I are added to the material to be stabilized in concentrations of from 0.01 to 5% by weight, preferably from 0.01 to 2% by weight, in particular from 0.1 to 1% by weight.

Owing to their rod-like structure, the compounds of the formula I are particularly suitable as stabilizers for liquid-crystalline individual components and liquid-crystal mixtures, since they interfere with the liquid-crystalline properties much less than do the anti-oxidants from the prior art.

Since the novel compounds have a particularly low vapor pressure, they can also be employed at high temperatures. They have properties similar to liquid crystals and do not cause discoloration in liquid-crystal mixtures. In contrast to known antioxidants, they do not have an adverse effect on the clearing point of the liquid-crystalline individual components.

The stabilization of the liquid crystals or liquid-crystal mixtures is carried out in a manner known per se. In general, all components are dissolved in one another, preferably at elevated temperature.

The novel stabilizers are preferably employed in STN liquid crystal mixtures containing tolans and alkenyls. The compounds of the formula I can also be added to the individual components, preferably alkenyls and tolans.

In particular, the novel stabilizers are suitable for suppressing decomposition and polymerization products of the following compounds.

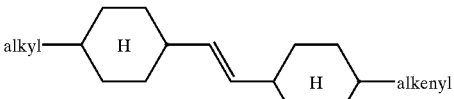

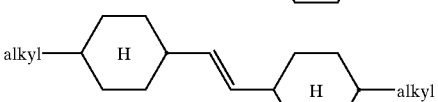

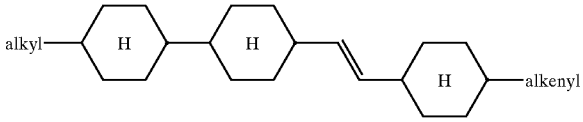

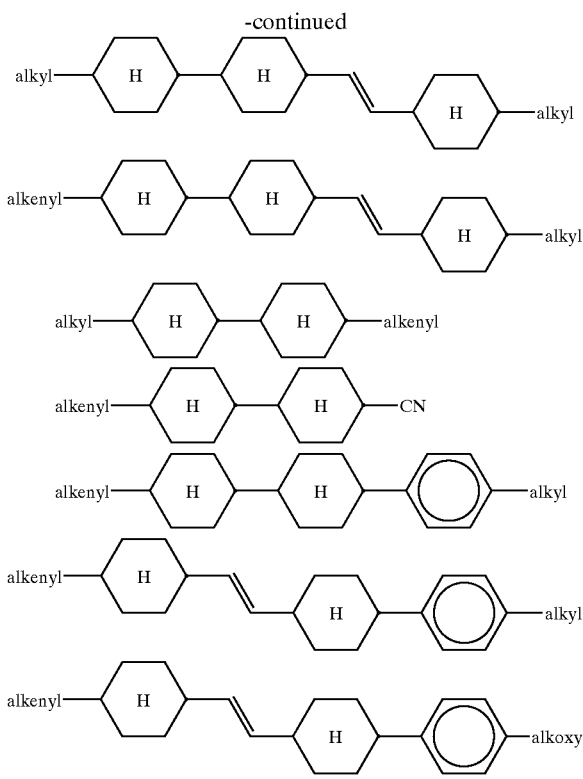

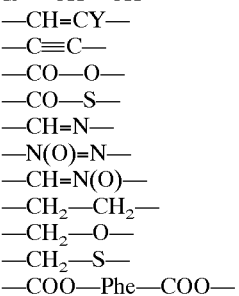

In such compounds, the double bond reacts particularly quickly with atmospheric oxygen. In particular, a double bond between two cyclohexane rings is sensitive to oxygen compared with a double bond in a side chain. The addition of from 0.01 to 5% by weight, in particular from 0.01 to 2% by weight, of a novel stabilizer, suppresses ageing processes initiated by $O_2$ free radicals from the air.

The invention also relates to a liquid-crystalline medium comprising at least two liquid-crystalline compounds and additionally a 2,6-di-tert-butylphenol of the formula I.

The invention furthermore relates to stable liquid-crystalline mixtures comprising at least one compound containing one or more double bonds and a stabilizer of the compound I.

The novel liquid-crystalline medium generally consists of from 2 to 25, preferably from 3 to 15, LC components and a stabilizer of the formula I. However, it is also possible in individual cases for more than 25 components to be constituents of a novel phase, for example up to 50 components or more. The other constituents are preferably selected from nematic or nematogenic substances, in particular known substances, from the classes consisting of the azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenyl- or cyclohexylpyrimidines, phenyl- or cyclohexyldioxanes, phenyl- or cyclohexyldithianes, 1,2-diphenylethanes, 1,2-dicyclohexylethanes, 1-phenyl-2-cyclohexylethanes, optionally halogenated stilbenes, benzyl phenyl ethers, tolans and substituted cinnamic acids.

The most important compounds which are suitable as constituents of liquid-crystalline phases of this type can be characterized by the formula II $$R^1—L—G—E—R^2 \qquad II$$

in which L and E are each a carbocyclic or heterocyclic ring system from the group consisting of 1,4-disubstituted benzene and cyclohexane rings, 2-fluoro-1,4-phenylene, 3-fluoro-1,4-phenylene, 2,6-difluoro-1,4-phenylene, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, G is —CH═CH—
—CH═CY—
—C≡C—
—CO—O—
—CO—S—
—CH═N—
—N(O)═N—
—CH═N(O)—
—CH₂—CH₂—
—CH₂—O—
—CH₂—S—
—COO—Phe—COO— or a C—C single bond, where Y is halogen, preferably chlorine, or —CN, and $R^1$ and $R^2$ unsubstituted or substituted by at least one or more fluoro atoms alkyl, alkoxy, alkanoyloxy or alkoxycarbonyloxy having 1 to 18, preferably 1 to 8, carbon atoms, or one of these radicals is alternatively CN, $NO_2$, $CF_3$, F, Cl or Br.

In most of these compounds, $R^1$ and $R^2$ are different from one another, one of these radicals usually being an alkyl or alkoxy group, and the other being alkyl, alkenyl, alkoxy, CN, F, Cl, $OCF_3$, $OCHF_2$, $OCH_2CF_3$, $OCHFCF_3$, $OCF_2CHFCF_3$, $OCH=CF_2$, $OCF=CF_2$ or $CH=CF_2$. However, other variants of the proposed substituents are also common. Many such substances or mixtures thereof are commercially available. All these substances can be prepared by methods which are known from the literature.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German application No. 195 39 141.1, filed Oct. 20, 1995 is hereby incorporated by reference.

In the present application and in the examples below, the structures of the liquid-crystal compounds are indicated by acronyms, with the transformation into chemical formulae taking place in accordance with Tables A and B below. All radicals $C_nH_{2n+1}$ and $C_mH_{2m+1}$ are straight-chain alkyl radicals having n or m carbon atoms respectively. The coding in Table B is self-evident. In Table A, only the acronym for the parent structure is given. In individual cases, the acronym for the parent structure is followed, separated by a dash, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |

| Code for $R^1$, $R^2$, $L^1$, $L^2$ | $R^1$ | $R^2$ | $L^1$ | $L^2$ |
|---|---|---|---|---|
| nF.F | $C_nH_{2n+1}$ | F | H | F |
| nF.F.F | $C_nH_{2n+1}$ | F | F | F |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}$—CH=$C_sH_{2s}$ | CN | H | H |
| rEsN | $C_rH_{2r+1}$—O—$C_sH_{2s}$ | CN | H | H |
| nAm | $C_nH_{2n+1}$ | COOC$_m$H$_{2m+1}$ | H | H |
| nOCCF$_2$.F.F | $C_nH_{2n+1}$ | OCH$_2$CF$_2$H | F | F |

Preferred mixture components are shown in Tables A and B.

TABLE A

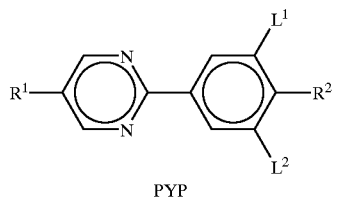

PYP

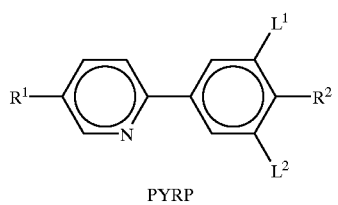

PYRP

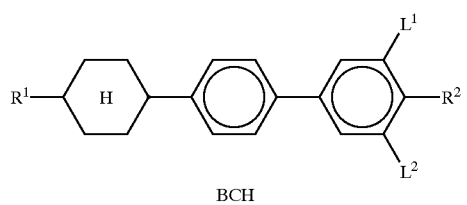

BCH

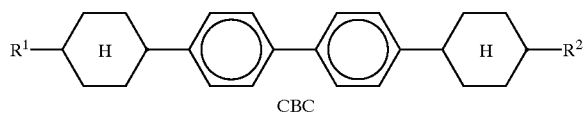

CBC

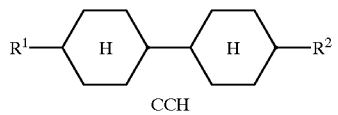

CCH

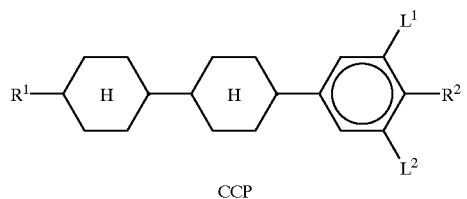

CCP

TABLE A-continued
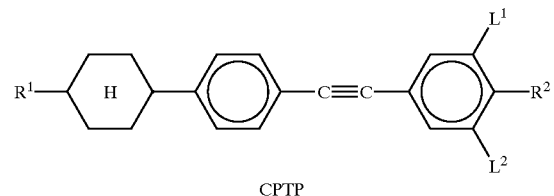
CPTP
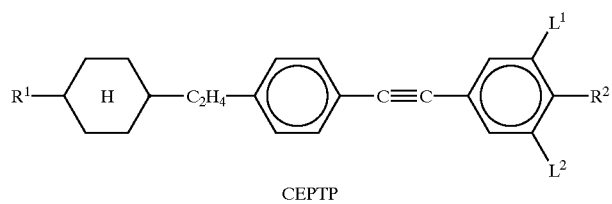
CEPTP
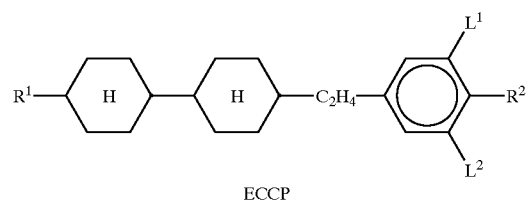
ECCP
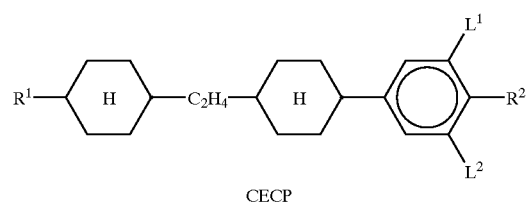
CECP
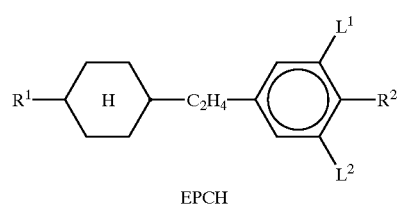
EPCH
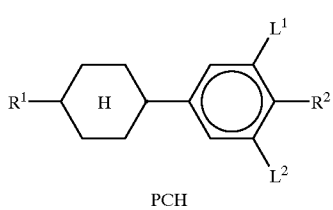
PCH
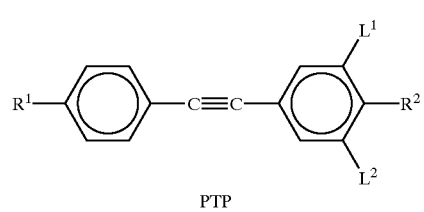
PTP TABLE A-continued
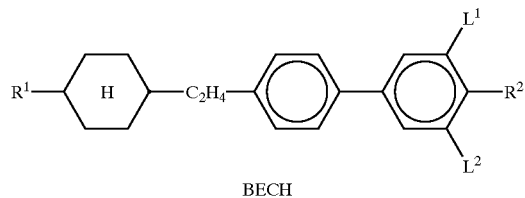
BECH
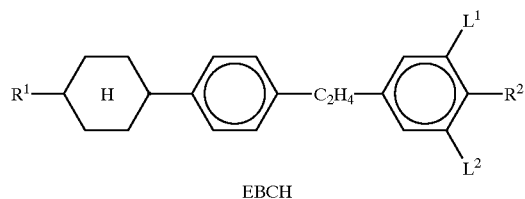
EBCH
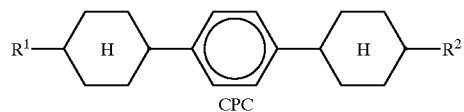
CPC
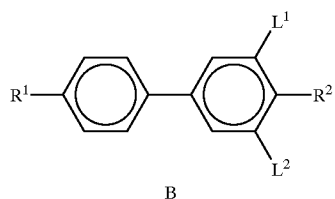
B
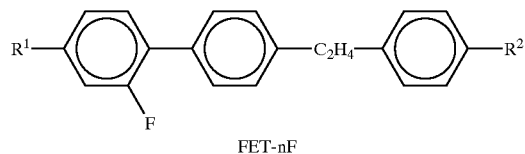
FET-nF
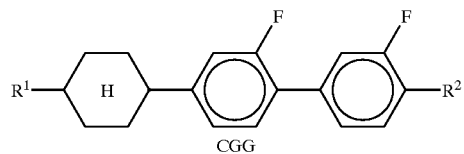
CGG
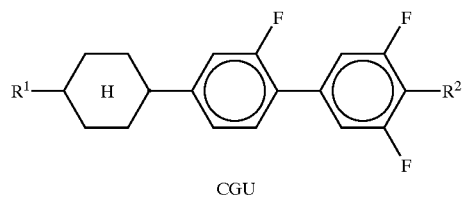
CGU
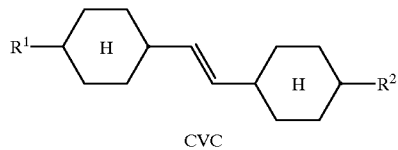
CVC TABLE B
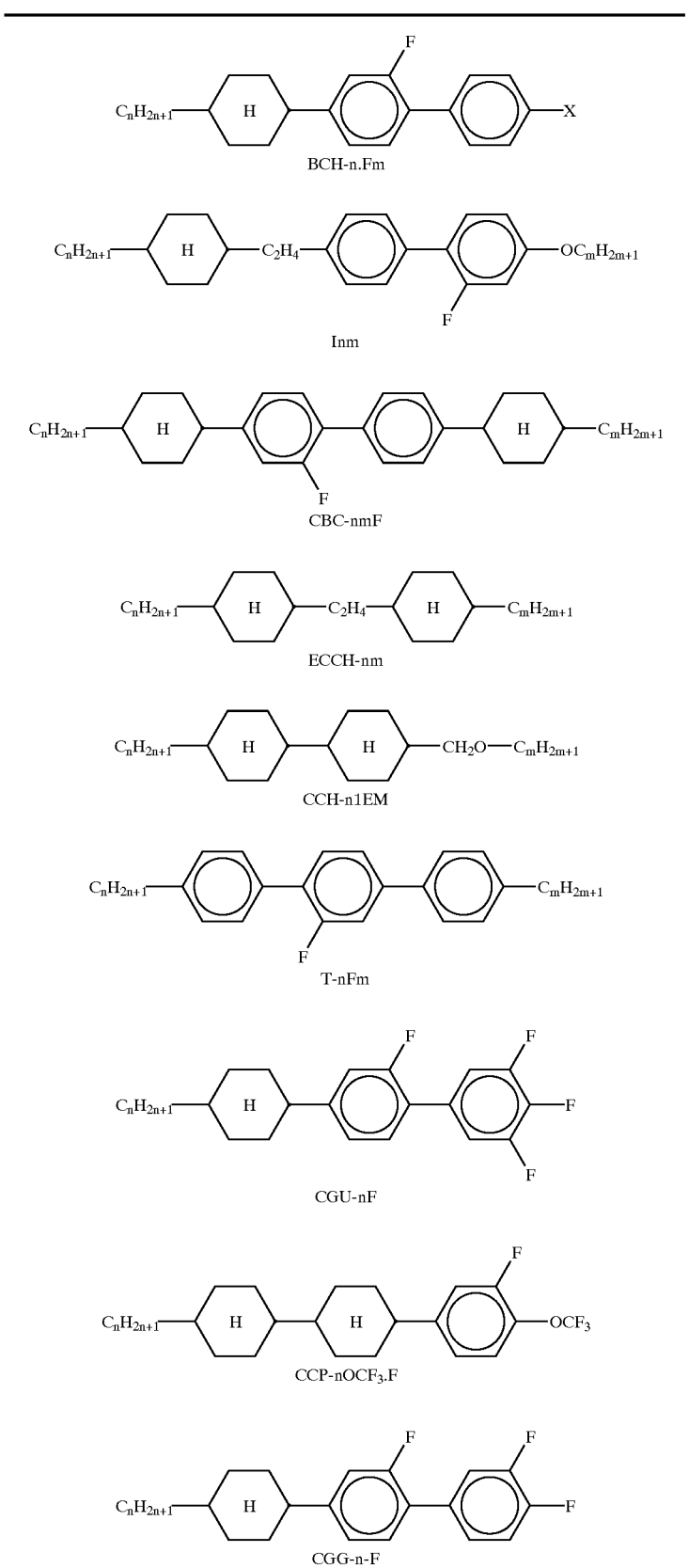

TABLE B-continued
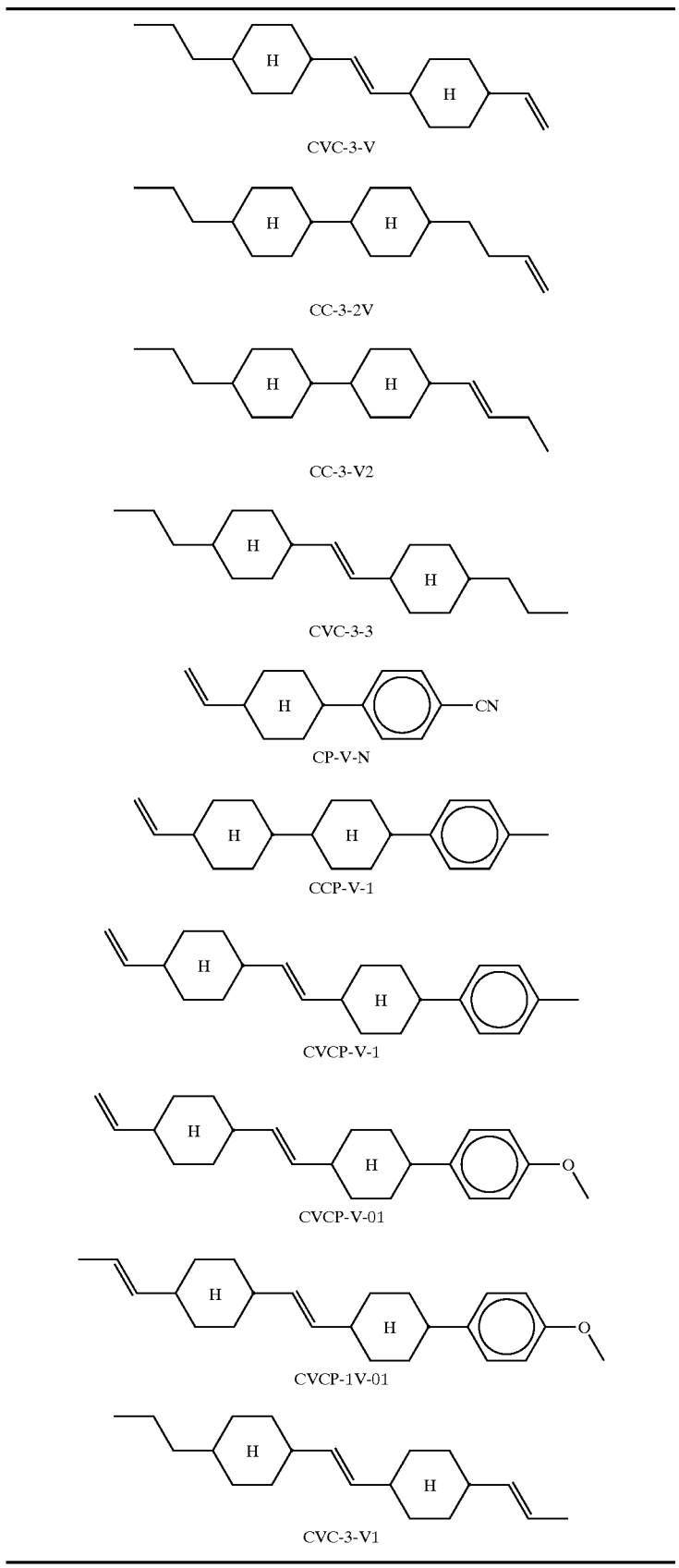

The examples below are intended to illustrate the invention without representing a limitation. "Conventional work-up" means that water is added, the mixture is extracted with dichloromethane, the organic phase is separated off, dried and evaporated, and the product is purified by crystallization and/or chromatography. Above and below, percentages are per cent by weight. All temperatures are given in degrees Celsius. m.p. denotes melting point and c.p.=clearing point. Furthermore, C=crystalline state, N=nematic phase, S=smectic phase and I=isotropic phase. The numbers between these symbols are the transition temperatures. An denotes the optical anisotropy (589 nm, 20° C.). The viscosity (mm²/sec) was determined at 20° C.

The following abbreviations are used:

| | |
|---|---|
| BuLi | butyllithium |
| DAST | diethylaminosulfur trifluoride |
| DCC | dicyclohexylcarbodiimide |
| DIBALH | diisobutylaluminum hydride |
| DMAP | 2-dimethylaminopyridine |
| DDQ | dichlorodicyanobenzoquinone |
| POT | potassium tert-butoxide |
| NH$_4$Cl | ammonium chloride |
| THF | tetrahydrofuran |
| TMDEA | tetramethylethylenediamine |
| pTsoH | p-toluenesulfonic acid |

I. EXAMPLES

Example 1

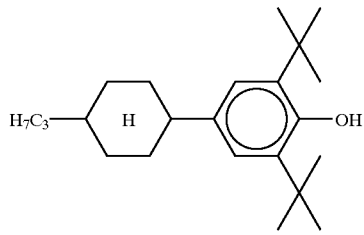

10.7 ml of conc. H$_2$SO$_4$ in 30 ml of glacial acetic acid are added dropwise at 0–5° C. with stirring to 0.1 mol of p-trans-(4-propylcyclohexyl)phenol in 0.2 mol of tert-butanol and 30 ml of glacial acetic acid. The mixture is left. to stir overnight at room temperature, water and methyl tert-butyl ether are added, and the organic phase is separated off, washed with NaHCO$_3$ solution and water and subjected to conventional work-up. The product is recrystallized from methanol. The compound gas a transition from crystalline to isotropic state at. 91° C. (i.e., C91I).

The following 2,6-di-tert-butylphenols of the formula

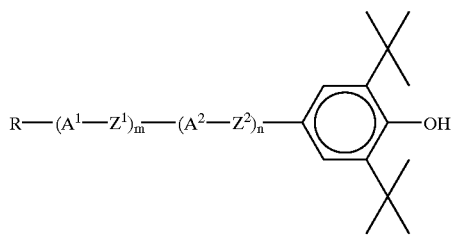

are prepared analogously:

| R | -(A$^1$-Z$^1$)$_m$-(A$^2$-Z$^2$)$_n$- |
|---|---|
| H | —⟨H⟩— |
| CH$_3$ | —⟨H⟩— |
| C$_2$H$_5$ | —⟨H⟩— |
| n-C$_4$H$_9$ | —⟨H⟩— |
| n-C$_5$H$_{11}$ | —⟨H⟩— |
| n-C$_6$H$_{13}$ | —⟨H⟩— |
| H | —⟨H⟩—⟨H⟩— |
| CH$_3$ | —⟨H⟩—⟨H⟩— |
| C$_2$H$_5$ | —⟨H⟩—⟨H⟩— |
| n-C$_4$H$_9$ | —⟨H⟩—⟨H⟩— |
| n-C$_5$H$_{11}$ | —⟨H⟩—⟨H⟩— |
| n-C$_6$H$_{13}$ | —⟨H⟩—⟨H⟩— |
| H | —⟨F⟩— |
| CH$_3$ | —⟨F⟩— |

-continued

| R | -(A¹-Z¹)ₘ-(A²-Z²)ₙ- |
|---|---|
| C₂H₅ | difluoro-phenyl |
| n-C₄H₉ | trifluoro-phenyl |
| n-C₅H₁₁ | trifluoro-phenyl |
| n-C₆H₁₃ | trifluoro-phenyl |
| H | cyclohexyl-phenyl |
| CH₃ | cyclohexyl-phenyl |
| C₂H₅ | cyclohexyl-phenyl |
| n-C₄H₉ | cyclohexyl-phenyl |
| n-C₅H₁₁ | cyclohexyl-phenyl |
| n-C₆H₁₃ | cyclohexyl-phenyl |
| H | biphenyl |
| CH₃ | biphenyl |

-continued

| R | -(A¹-Z¹)ₘ-(A²-Z²)ₙ- |
|---|---|
| C₂H₅ | biphenyl |
| n-C₄H₉ | biphenyl |
| n-C₅H₁₁ | biphenyl |
| n-C₆H₁₃ | biphenyl |
| H | dicyclohexyl-C₂H₄ |
| CH₃ | dicyclohexyl-C₂H₄ |
| C₂H₅ | dicyclohexyl-C₂H₄ |
| n-C₄H₉ | dicyclohexyl-C₂H₄ |
| n-C₅H₁₁ | dicyclohexyl-C₂H₄ |
| n-C₆H₁₃ | dicyclohexyl-C₂H₄ |
| H | dioxanyl-cyclohexyl |
| CH₃ | dioxanyl-cyclohexyl |
| C₂H₅ | dioxanyl-cyclohexyl |
| n-C₄H₉ | dioxanyl-cyclohexyl |

| R | -(A$^1$-Z$^1$)$_m$-(A$^2$-Z$^2$)$_n$- |
|---|---|
| n-C$_5$H$_{11}$ | [1,3-dioxane-cyclohexane] |
| n-C$_6$H$_{13}$ | [1,3-dioxane-cyclohexane] |
| H | [1,3-dioxane] |
| CH$_3$ | [1,3-dioxane] |
| C$_2$H$_5$ | [1,3-dioxane] |
| n-C$_4$H$_9$ | [1,3-dioxane] |
| n-C$_5$H$_{11}$ | [1,3-dioxane] |
| n-C$_6$H$_{13}$ | [1,3-dioxane] |
| H | [cyclohexane-1,3-dioxane] |
| CH$_3$ | [cyclohexane-1,3-dioxane] |
| C$_2$H$_5$ | [cyclohexane-1,3-dioxane] |
| n-C$_4$H$_9$ | [cyclohexane-1,3-dioxane] |
| n-C$_5$H$_{11}$ | [cyclohexane-1,3-dioxane] |
| n-C$_6$H$_{13}$ | [cyclohexane-1,3-dioxane] |

| R | -(A$^1$-Z$^1$)$_m$-(A$^2$-Z$^2$)$_n$- |
|---|---|
| H | [pyridine] |
| CH$_3$ | [pyridine] |
| C$_2$H$_5$ | [pyridine] |
| n-C$_4$H$_9$ | [pyridine-phenyl] |
| n-C$_5$H$_{11}$ | [pyridine-phenyl] |
| n-C$_6$H$_{13}$ | [pyridine-phenyl] |
| H | [pyrimidine] |
| CH$_3$ | [pyrimidine] |
| C$_2$H$_5$ | [pyrimidine] |
| n-C$_4$H$_9$ | [phenyl-pyrimidine] |
| n-C$_5$H$_{11}$ | [phenyl-pyrimidine] |
| OC$_5$H$_{11-n}$ | [phenyl-pyrimidine] |
| H | [pyrimidine-phenyl] |
| CH$_3$ | [pyrimidine-phenyl] |

-continued

| R | $-(A^1-Z^1)_m-(A^2-Z^2)_n-$ |
|---|---|
| $C_2H_5$ | pyrimidine-phenyl |
| n-$C_4H_9$ | pyrimidine-phenyl |
| n-$C_5H_{11}$ | pyrimidine-phenyl |
| n-$C_6H_{13}$ | pyrimidine-phenyl |

II. STABILITY TESTS

2.1 Heat and UV Stability Under Standard Conditions

The following alkenyls were tested under standard conditions (T=150° C., under $N_2$ for 100 h):

| Acronym | Structure |
|---|---|
| CVC-3V | (structure) |
| CC-3-2V | (structure) |
| CC-3-V2 | (structure) |

All alkenyls were heat- and UV-stable. Gaschromatographic analysis showed no decomposition or polymerization products.

2.2 Stability Tests of Alkenyls in the Presence of Oxygen

The tests were carried out in a standard host at 80° C. The host selected was a 1:1 mixture of I32 and I52 owing to the broad nematic phase range.

2.2.1 Three different alkenyls were added, in an amount of 10% in each case, to the standard host, and the mixture was then stirred in an open flask at 80° C. for 11 h.

% by weight (GLC) of the compounds before and after heat treatment

| Acronym | Structure | 0 h | 4 h | 11 h |
|---|---|---|---|---|
| CVC-3-V | (structure) | 10.1 | 9.6 | 7.7 |
| CC-3-2V | (structure) | 10.3 | 9.9 | 9.8 |
| CC-3-V2 | (structure) | 9.9 | 9.8 | 8.5 |
| I32 (host) | (structure) | 35.2 | 35.7 | 33.8 |

-continued

| | % by weight (GLC) of the compounds before and after heat treatment | | | |
|---|---|---|---|---|
| Acronym | Structure | 0 h | 4 h | 11 h |
| I52 (host) | (structure) | 34.0 | 34.1 | 33.2 |

2.2.2 Investigation of the heat stability of individual compounds in the presence or absence of an antioxidant (0.1% BHT)

Experimental conditions: 20% of the compounds in the host 80° C. at 100 h (without stirring)
Host: I32/I52 (1:1)
Reference: CCH-34

| | | Content of compounds [%] (GLC) after | | | | | |
|---|---|---|---|---|---|---|---|
| Time (h) | | 0 | 25 | 50 | 100 | 200 | 400 |
| (structure) | A | 22.2 | 22.0 | 22.1 | 22.1 | 21.8 | 21.9 |
| | B | 22.0 | 22.1 | 22.0 | 22.0 | 21.7 | 21.7 |
| (structure) | A | 21.1 | | 21.1 | 21.3 | 21.2 | 21.3 |
| | B | 21.2 | | 21.1 | 21.1 | 21.5 | 21.1 |
| (structure) | A | 19.7 | | 19.8 | 19.7 | 19.4 | 18.1 |
| | B | 20.7 | | 20.2 | 20.5 | 20.0 | 20.0 |
| (structure) | A | 60.4 | | 59.0 | 56.4 | 50.7 | |
| | B | 60.5 | | 60.5 | 60.7 | 60.7 | 60.4 |

-continued
| | Content of compounds [%] (GLC) after | | | | | | |
|---|---|---|---|---|---|---|---|
| Time (h) | | 0 | 25 | 50 | 100 | 200 | 400 |
| 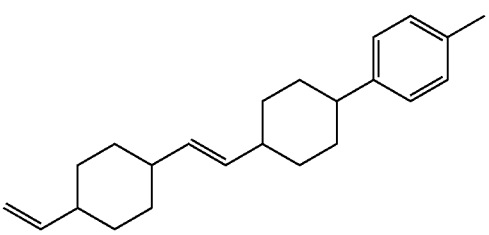 | A<br>B | 20.5<br>20.9 | | 19.2<br>21.0 | 16.3<br>20.9 | 7.7<br>20.8 | <br>20.9 |
| 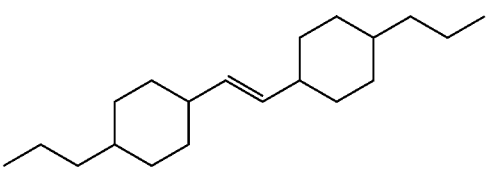 | A<br>B | 20.6<br>20.6 | | 19.0<br>20.4 | 15.1<br>20.4 | 8.2<br>20.2 | <br>20.2 |
| 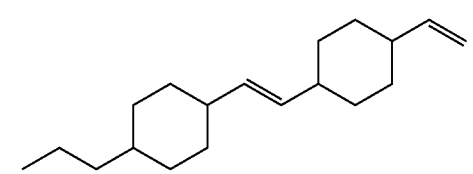 | A<br>B | 19.6<br>21.7 | 18.5 | 18.1<br>21.5 | 14.1<br>21.7 | 5.9<br>21.3 | <br>19.9 |
| 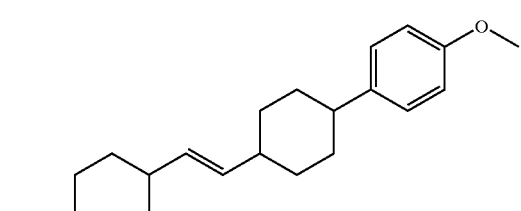 | A<br>B | 20.0<br>20.0 | | 19.6<br>20.2 | 19.1<br>20.2 | 17.6<br>20.2 | <br>20.0 |
| 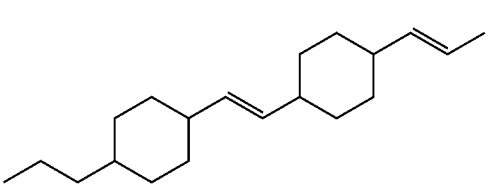 | A<br>B | 22.1<br>21.9 | 21.2 | 19.8<br>21.9 | 14.2<br>22.0 | 4.8<br>21.7 | <br>21.6 |
| 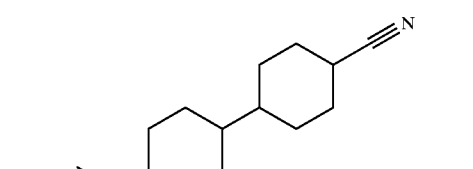 | A<br>B | 20.4<br>20.6 | | 20.5<br>20.6 | 19.9<br>20.5 | 17.9<br>20.4 | <br>20.3 |
| 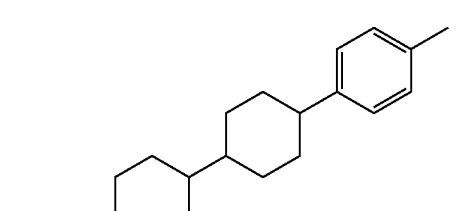 | A<br>B | 20.6<br>20.6 | | 20.2<br>20.6 | 19.9<br>20.8 | 17.0<br>20.5 | <br>20.5 |

-continued
| | | Content of compounds [%] (GLC) after | | | | | |
|---|---|---|---|---|---|---|---|
| Time (h) | | 0 | 25 | 50 | 100 | 200 | 400 |
| 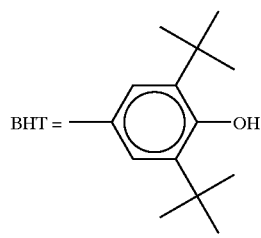 | A | 21.1 | | 21.1 | 20.5 | 18.8 | |
| | B | 21.5 | | 21.4 | 21.3 | 21.3 | 21.3 |
A: without BHT
B: with 0.1% BHT
BHT = 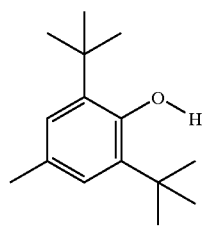
2.2.3 Effect of Various Stabilizers on the Oxidation of CVC-3-V1
Experimental conditions: 20% of CVC-3-V1 in the host, 80° C., open flask (without stirring)
Host: I32+I52 (1:1)
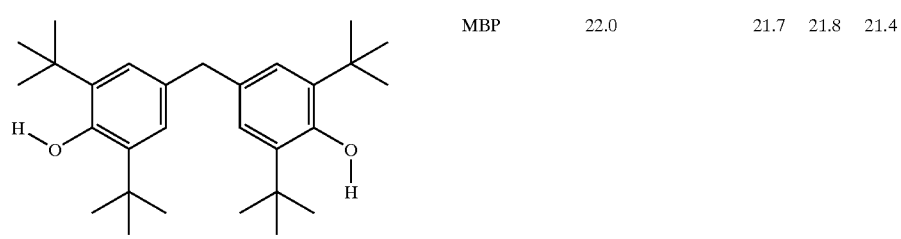
| Stabilizer | Name | Content of CVC-3-V1 after | | | | | |
|---|---|---|---|---|---|---|---|
| | | 0 h | 25 h | 50 h | 100 h | 200 h | 400 h |
| none | | 21.9 | 20.4 | 17.3 | 12.2 | | |
| | BHT | 21.9 | | | 21.8 | 21.8 | 21.7 |
| | MBP | 22.0 | | | 21.7 | 21.8 | 21.4 |

-continued

| Stabilizer | Name | Content of CVC-3-V1 after | | | | | |
|---|---|---|---|---|---|---|---|
| | | 0 h | 25 h | 50 h | 100 h | 200 h | 400 h |
| 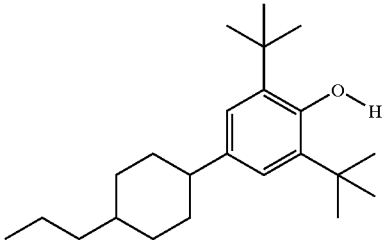 INVENTION | | 22.0 | | | 21.7 | 21.7 | 21.4 |
| 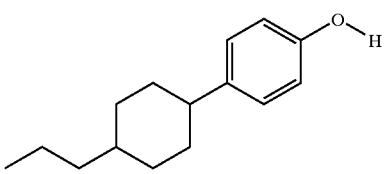 | PCH-3-OH | 21.8 | | | 21.6 | 19.7 | 5.9 |
| 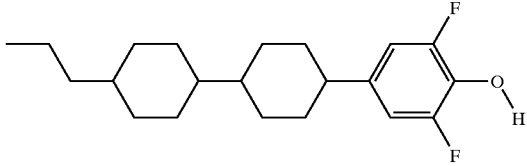 | CCU-3-OH | 22.0 | | 21.3 | 20.6 | 14.6 | 1.2 |

LC mixtures stabilized with MBP yellow with time.
BHT is readily volatile and therefore difficult to handle.

2.2.4 Effect of the Content of Various Stabilizers on the Oxidation of CVC-3-V1

Experimental conditions:
  20% of CVC-3V1 in the standard host (I32:I52=1:1)
  Temperature: 80° C.
  open flask, no stirring

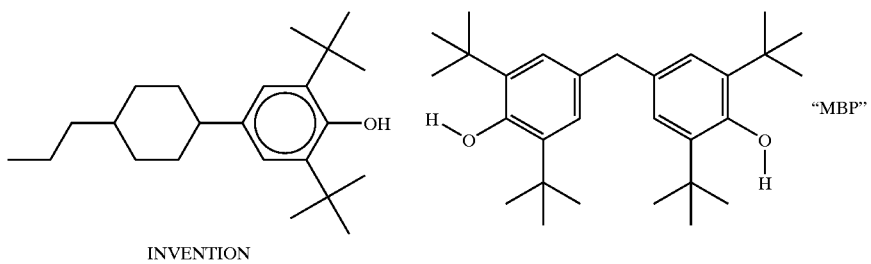

INVENTION                                   "MBP"

| | Stabilizer content [%] | | | | Stabilizer content [%] | | |
|---|---|---|---|---|---|---|---|
| | 0.1 | 0.05 | 0.01 | | 0.1 | 0.05 | 0.01 |
| 0 h | 22.0 | 22.0 | 21.9 | 0 h | 22.0 | 22.1 | 22.1 |
| 25 h | 21.9 | 21.9 | 22.0 | 25 h | 22.0 | 22.1 | 22.0 |
| 50 h | 21.9 | 22.0 | 21.9 | 50 h | 21.9 | 21.9 | 21.9 |
| 100 h | 21.9 | 22.0 | 21.9 | 100 h | 22.0 | 22.1 | 22.1 |
| 175 h | 21.8 | 21.9 | 21.7 | 175 h | 21.9 | 21.9 | 22.0 |
| 250 h | 21.9 | 21.9 | 21.8 | 250 h | 21.8 | 21.9 | 21.9 |
| 400 h | 21.8 | 21.9 | 20.8* | 400 h | 21.7 | 21.9 | 20.6* |

-continued

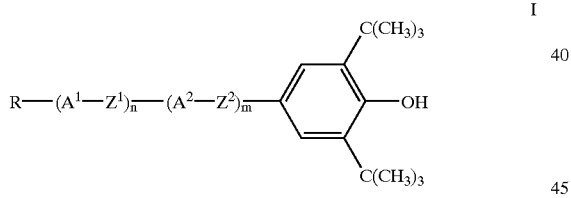

"MBP", purified none

| | Stabilizer content [%] | | | | Stabilizer content [%] |
|---|---|---|---|---|---|
| | 0.1 | 0.05 | 0.01 | | |
| Time | CVC-3-V1 content [%] | | | Time | CVC-3-V1 content [%] |
| 0 h | 22.0 | 22.1 | 22.0 | 0 h | 22.2 |
| 25 h | 22.2 | 22.1 | 22.1 | 25 h | 21.5* |
| 50 h | 21.9 | 22.0 | 22.3 | 50 h | 20.4* |
| 100 h | 21.9 | 22.0 | 22.2 | 100 h | 16.4* |
| 175 h | 21.8 | 21.9 | 21.8 | 175 h | 9.5* |
| 250 h | 22.0 | 21.9 | 21.9 | 250 h | 5.2* |
| 400 h | 22.1 | 22.0 | 21.3* | 400 h | 0.9* |

MBP: yellowed, MBP purified: recrystallized twice from hexane, still slightly yellowish. Both LC mixtures containing MBP were yellow after 400 h.
*indicates beginning or continuing decomposition.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A 2,6-di-tert-butylphenol of the formula I $$R-(A^1-Z^1)_{\overline{n}}-(A^2-Z^2)_{\overline{m}}-\text{[2,6-di-tert-butylphenol ring with OH]} \quad I$$

in which
R is a straight chain alkyl radical having 1 to 18 carbon atoms which is unsubstituted and in which one or more non-adjacent $CH_2$ groups are optionally replaced by a radical selected from the group consisting of —O—, —CO— and —C≡C—, $A^1$ and $A^2$ are, independently of one another,
a) a 1,4-phenylene radical, in which one or two CH groups are optionally replaced by N, or
b) a 1,4-cyclohexenylene or 1,4-cyclohexylene radical, in which one or two non-adjacent $CH_2$ groups are optionally replaced by —O— or —S—,
wherein the radical a) is optionally monosubstituted or polysubstituted by halogen atoms, and/or cyano groups, and radical b) is optionally monosubstituted or polysubstituted by halogen atoms, and/or cyano and/or methyl groups, $Z^1$ and $Z^2$ are each, independently of one another, —CO—O—, —O—CO—, —$CH_2$—O—, —O$CH_2$—, —$CH_2CH_2$—, —CH=CH—, —C≡C— or a single bond, and m and n are each, independently of one another 0, 1, 2 or 3, where m+n≧1, with the proviso that compounds of the formulae

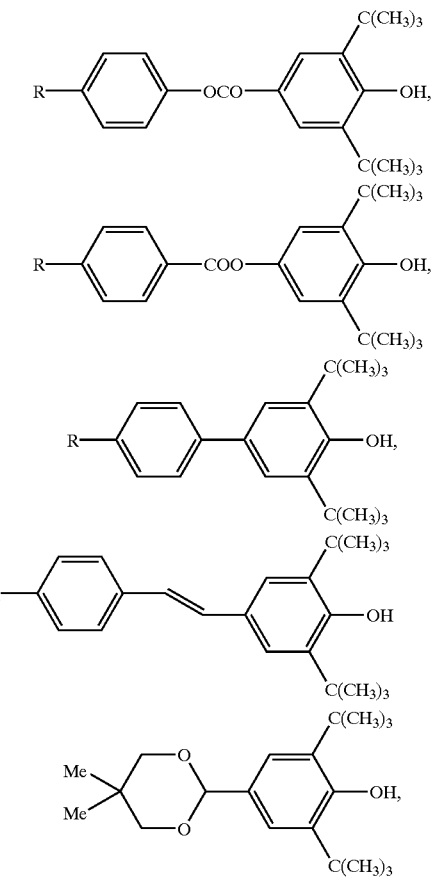

each where R=—C≡CH, alkyl or alkyl with the $CH_2$ group bonded to the ring replaced by —O— or —CO— and each where the phenyl rings are optionally further substituted by chlorine or bromine atoms, are excluded.

2. A 2,6-di-tert-butylphenol of the formula I1

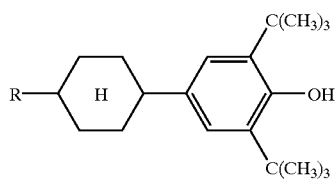

in which

R is an alkyl or alkenyl radical having 1 to 18 carbon atoms which is unsubstituted or substituted by CN or by at least one halogen, and in which one or more non-adjacent $CH_2$ groups are optionally replaced by a radical selected from the group consisting of —O—, —S—, —CO—, —O—CO—, —CO—O— and —C≡C—.

3. A method for stabilizing a composition which comprises adding to the composition a 2,6-di-tert-butylphenol according to claim 1.

4. The method of claim 3, wherein the composition is a liquid crystalline composition.

5. A liquid-crystalline medium comprising at least two liquid-crystalline compounds and at least one 2,6-di-tert-butylphenol according to claim 1.

6. A liquid-crystalline medium according to claim 5, comprising from 0.01 to 5% by weight of the at least one 2,6-di-tert-butylphenol.

7. An electrooptical display containing a liquid-crystalline medium according to claim 5.

8. The 2,6-di-tert-butylphenol of claim 1, wherein n+m is 1 or 2.

9. A 2,6-di-tert-butylphenol of one of the formulae I1 to I10:

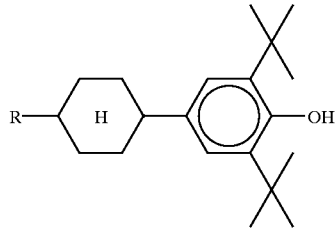

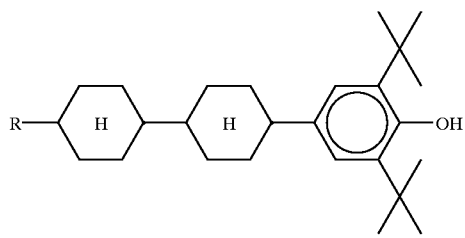

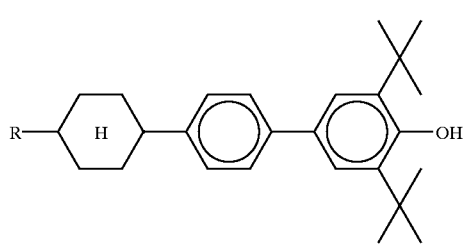

-continued

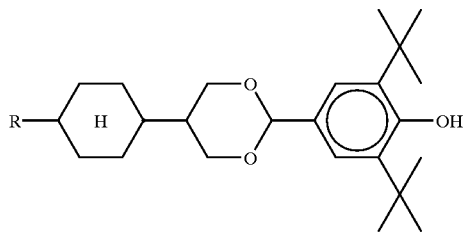

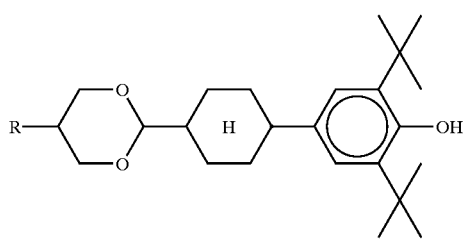

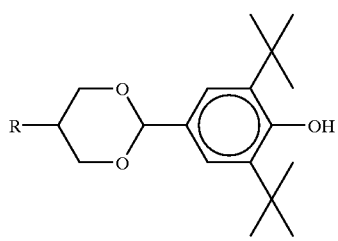

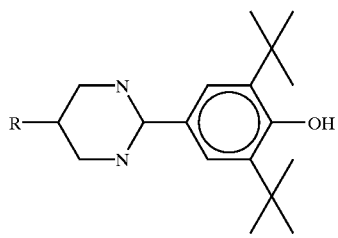

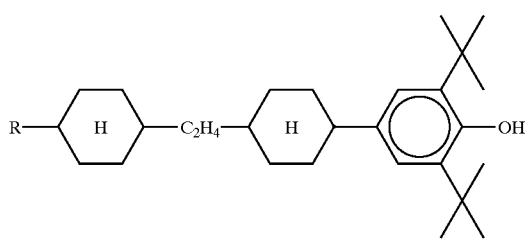

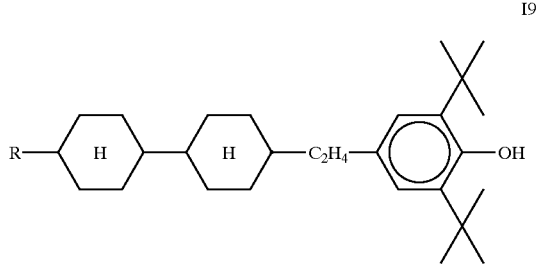

-continued

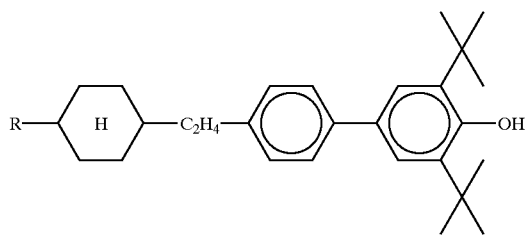

I10 wherein
R is an alkyl or alkenyl radical having 1 to 18 carbon atoms which unsubstituted or substituted by CN or by at least one halogen, and in which one or more non-adjacent CH$_2$ groups are optionally replaced by a radical selected from the group consisting of —O—, —S—, —CO—, —O—CO—, —CO—O— and —C≡C—.

10. The method of claim 4, wherein the liquid crystalline medium comprises a tolan liquid crystalline compound and/or an alkenyl-group containing liquid crystalline compound, which is not the 2,6-di-tert-butylphenol.

* * * * *

UNITED STATES PATENT AND TRADEMARK OFFICE
CERTIFICATE OF CORRECTION

PATENT NO.   : 6,444,278 B1
DATED        : September 3, 2002
INVENTOR(S)  : Volker Reiffenrath et al.

It is certified that error appears in the above-identified patent and that said Letters Patent is hereby corrected as shown below:

<u>Title page,</u>
Item [75], Inventors, reads "Darmstadt" should read -- Rossdorf --; and reads "Darmstadt" should read -- Dieburg --

<u>Column 42,</u>
Line 3, reads "which unsubstituted" should read -- which is unsubstituted --

Signed and Sealed this

Third Day of May, 2005

JON W. DUDAS
*Director of the United States Patent and Trademark Office*